United States Patent
Ouellette (10) Patent No.: US 9,470,657 B2
(45) Date of Patent: Oct. 18, 2016

(54) MEASUREMENT OF LAY LENGTH OF WIRE ROPE

(71) Applicant: Her Majesty the Queen in Right of Canada as Represented by the Minister of Natural Resources Canada, Ottawa (CA)

(72) Inventor: Sylvain Ouellette, Val-d'Or (CA)

(73) Assignee: Her Majesty the Queen in Right of Canada as Represented by the Minister of Natural Resources Canada (CA)

( * ) Notice: Subject to any disclaimer, the term of this patent is extended or adjusted under 35 U.S.C. 154(b) by 23 days.

(21) Appl. No.: 14/433,422

(22) PCT Filed: Oct. 4, 2012

(86) PCT No.: PCT/CA2012/050701
§ 371 (c)(1),
(2) Date: Apr. 3, 2015

(87) PCT Pub. No.: WO2014/053047
PCT Pub. Date: Apr. 10, 2014

(65) Prior Publication Data

US 2015/0285767 A1   Oct. 8, 2015

(51) Int. Cl.
*G01N 27/82* (2006.01)
*G01R 33/04* (2006.01)
(Continued)

(52) U.S. Cl. (Continued)
CPC .............. *G01N 27/82* (2013.01); *D07B 1/145* (2013.01); *G01B 7/046* (2013.01); *G01R 33/04* (2013.01);
(Continued)

(58) Field of Classification Search
CPC ...... G01N 27/82; G01N 27/83; G01N 27/90; G01N 27/9013; G01N 27/9026; G01N 27/9033; G01N 27/904; G01N 27/72; G01R 33/00; G01R 33/0035; G01R 33/0047; G01R 33/0322; G01R 33/0327; G01R 33/10; G01R 33/1284
USPC ........... 324/51, 55, 200, 217, 219, 228, 233, 324/239, 240, 254, 257, 260
See application file for complete search history.

(56) References Cited

U.S. PATENT DOCUMENTS

| 4,507,610 A | 3/1985 | Nakaoka |
| 4,659,991 A | 4/1987 | Weischedel |

(Continued)

FOREIGN PATENT DOCUMENTS

| GB | 2183044 A | 5/1987 |
| WO | 2010077840 A2 | 7/2010 |
| WO | 2011112734 A1 | 9/2011 |

OTHER PUBLICATIONS

May 17, 2013 (PCT) International Search Report—App PCT/CA2012/050701.

*Primary Examiner* — Jermele M Hollington
*Assistant Examiner* — Raul Rios Russo
(74) *Attorney, Agent, or Firm* — Banner & Witcoff, Ltd.

(57) ABSTRACT

The invention relates to a method and apparatus for measuring lay length of a wire rope having a number or external strands to form a rope having spiral grooves in the surface between the strands. A magnetic flux circuit is generated, part of which is formed within a region of the advancing wire rope. Variations of magnetic field around the region of the rope or variations of magnetic flux entering or leaving the rope are sensed by at least two sensors arranged around the rope. Signals from the sensors are subtractively combined to eliminate variations due to off-axis movements of the rope, and the combined signals reveal an oscillating pattern due to the undulating surface of the rope. Linking the oscillating pattern to distance along the rope reveals the lay length, which corresponds to a number of oscillations which is the same as the number of strands at the surface.

36 Claims, 6 Drawing Sheets

(51) Int. Cl.
  *G01R 33/07* (2006.01)
  *G01B 7/04* (2006.01)
  *D07B 1/14* (2006.01)
  *G01N 27/90* (2006.01)
  *G01N 27/83* (2006.01)

(52) U.S. Cl.
  CPC ....... *G01R 33/07* (2013.01); *D07B 2201/2026* (2013.01); *D07B 2301/251* (2013.01); *D07B 2301/45* (2013.01); *D07B 2301/555* (2013.01); *D07B 2501/2007* (2013.01); *G01N 27/83* (2013.01); *G01N 27/90* (2013.01)

(56) References Cited

U.S. PATENT DOCUMENTS

| | | |
|---|---|---|
| 4,827,215 A | 5/1989 | van der Walt |
| 5,321,356 A | 6/1994 | Weischedel |
| 5,402,066 A | 3/1995 | Hickman, Jr. et al. |
| 5,414,353 A | 5/1995 | Weischedel |
| 5,589,772 A | 12/1996 | Kugai |
| 5,729,135 A | 3/1998 | Kugai |
| 5,777,469 A | 7/1998 | Hockey et al. |
| 5,804,964 A | 9/1998 | Hamelin et al. |
| 5,828,213 A | 10/1998 | Hickman |
| 5,986,452 A | 11/1999 | Hockey et al. |
| 6,150,809 A | 11/2000 | Tiernan et al. |
| 6,728,453 B2 | 4/2004 | Petryszak |
| 8,058,881 B2 | 11/2011 | Engbring et al. |
| 8,098,065 B2 | 1/2012 | Kwun et al. |
| 2003/0042897 A1 | 3/2003 | Wolodko |
| 2009/0232383 A1 | 9/2009 | Verreet |
| 2010/0043381 A1* | 2/2010 | Van Zyl ................. D07B 1/068 57/215 |
| 2010/0102807 A1* | 4/2010 | Yoshioka ............... G01N 27/83 324/240 |
| 2010/0148766 A1 | 6/2010 | Weischedel |
| 2011/0219610 A1 | 9/2011 | Cornelison |
| 2011/0268313 A1 | 11/2011 | Winter et al. |
| 2012/0038357 A1 | 2/2012 | Brandon et al. |
| 2013/0024135 A1 | 1/2013 | Blum |
| 2013/0147471 A1* | 6/2013 | Weischedel ............ G01N 27/83 324/238 |

* cited by examiner

MEASUREMENT OF LAY LENGTH OF WIRE ROPE

RELATED APPLICATION DATA

This application is a National Stage Application under 35 U.S.C. 371 of co-pending PCT application number PCT/CA2012/050701 designating the United States and filed Oct. 4, 2012 which is hereby incorporated by reference in its entirety.

TECHNICAL FIELD

This invention relates to the measurement of lay length of wire ropes. More particularly, the invention relates to methods and apparatus for carrying out such measurements while the wire ropes are in use and under tension.

BACKGROUND ART

Wire ropes are used for many purposes such as ropeways, cable cars, ski lifts, chairlifts and elevators, but are of particular importance in the mining industry where they are used for raising and lowering conveyances holding miners, equipment and ore between the mining galleries and the surface. For such applications, wire ropes often have to be of considerable length, e.g. 10,000 feet or more, and must carry considerable loads, including the weight of the ropes themselves in the sections between the conveyances and the mine hoists at the surface used for their deployment.

To ensure operational safety and long operational life of the equipment, the physical condition of such ropes must be monitored frequently and the ropes must be replaced often. An important parameter that indicates rope condition is the so-called "lay length". Wire ropes are made up of twisted or braided metal wires. Individual metal wires are twisted together to form wire bundles or strands, and then a number of such strands are twisted together to form a rope. The lay length of such a rope is the distance along the rope (measured parallel to the center line or axis of the rope) in which a strand at the surface makes one complete turn or spiral around the rope. Often, the lay length is measured over a few lay lengths (e.g. four) and then the measurement is divided by the number of lay lengths to produce an average lay length value over the measured section. The lay length is known when a rope is first manufactured (or at least after the strands have been allowed to settle into their permanent positions following a few lifting cycles) but it will change during use. In mining applications, the lay length of a rope naturally changes with depth due to the torsional behaviour of stranded hoist rope. These natural variations evolve during the life of the rope and must be monitored to ensure that they remain within established limits. Local variations also occur in the rope at crossover points and can also occur due to localized faults as a result of a number of causes, e.g. corrosion, core deterioration, wire breakage, rope rotation (i.e. strand unlaying), or physical contacts. The relevance of changes of lay length of a rope requires expert interpretation. In general, however, if the lay length of a rope or a section of a rope changes beyond defined limits, or if it changes locally, this may indicate potential failure of the rope, requiring a need for rope replacement.

One known method of measuring lay length is to take the rope out of service and to measure the lay length with direct measuring devices. Naturally, this involves a shutdown of the operating equipment and can therefore be done only infrequently. Furthermore, direct measurement of the lay length of an entire rope is difficult and prone to error because of the lengths of such ropes. On the other hand, measurement of lay length when the rope is in place in lifting apparatus, and especially when the rope is in use, is also difficult, especially because the rope may be covered in grease, dirt and/or provided with a protective cover or sheath made of plastics or other material, thereby obscuring the strands from visual inspection. This is a problem for equipment that relies on the use of photographic imaging or other visual means, such as that disclosed in US published patent application No. 2009/0232383 A1 to Roland Verreet published on Sep. 17, 2009, or published International patent application WO 2011/112734 to Cornelison et al. published on Sep. 15, 2011.

Another approach to monitoring rope condition has relied on the magnetic or electrically-conductive properties of metal ropes which are normally made of electrically-conductive and magnetically-permeable materials. In fact they are almost always made of steel. U.S. Pat. No. 8,058,881 B2 which issued to Engbring et al. on Nov. 15, 2011, discloses a method of measuring a fault in a braided wire by passing an electric current through the braided wire, using a sensor to detect the magnetic field produced by the current, and deducing the location of a fault in the braided wire when the measured magnetic field has a characteristic oscillation corresponding to the lay length or a multiple thereof. However, this device does not measure the lay length of the braided wire, but rather makes an assumption of the lay length to detect a fault.

It is also known to use magnetic properties to measure other rope conditions, e.g. local faults and loss of metallic area of the rope. An example is disclosed in U.S. Pat. No. 5,804,964 which issued to Hamelin et al. on Sep. 8, 1998. This patent discloses a device having a permanent magnet assembly encircling and creating a magnetic flux in the rope, and employing Hall effect sensors and leakage flux sensors to produce a numerical damage index for the rope in real time.

Nevertheless, there is a need for a way of measuring rope lay length, especially when the rope is under tension and in movement in an operating environment.

DISCLOSURE OF THE INVENTION

In one exemplary embodiment, the invention provides a method of measuring lay length of a wire rope. The method involves advancing a wire rope in a direction of a central axis of the rope while permitting limited transverse movements of the wire rope, the wire rope having a number of spirally wound external strands with grooves between the strands causing the rope to have a spirally grooved outer surface undulating in surface height from the central axis, and having lay length over which each of the strands completes a single circumferential spiral path around the central axis of the wire rope. A magnetic flux circuit is established, part of which magnetic flux circuit occupies a region of the advancing wire rope. Changes of magnetic field strength or magnetic flux are sensed in the stated region of the rope due to variations of proximity of the wire rope from fixed positions spaced circumferentially around the wire rope, the positions being radially aligned with points on the wire rope at which the surface heights of the wire rope differ most of the time due to the undulating surface, and signals corresponding to changes of magnetic field or magnetic flux sensed at these positions are generated, the signals each including components due to surface height and components due to lateral movements of the wire rope at the positions. The signals are subtractively combined (i.e. subtracted one from another, e.g. by one signal being made positive and the other negative when combined) to eliminate the components due to the lateral movements to thereby produce a combined signal having an oscillating pattern caused by differences of surface height at the fixed positions. Oscillations in the pattern are associated with physical distances along the wire rope and the lay length of the wire rope is established as a distance along the wire rope of a plurality of the oscillations corresponding in number to the number of spirally wound external strands of the wire rope.

Thus, as the surface of the wire rope advances towards or recedes away from a fixed point due to its undulating shape and due to any lateral (off-axis) movements of the wire rope, the magnetic field surrounding the region of the wire rope containing part of the magnetic flux circuit varies at a fixed position and such variations can be sensed. Also, at points where the magnetic flux enters or leaves the region of the wire rope to complete the magnetic flux circuit, the strength of the magnetic flux entering or leaving the rope across a gap (e.g. a gap between the wire rope and confronting metal pole pieces) varies as the surface of the rope advances towards or recedes from such fixed point, and the variations of magnetic flux can be sensed. These sensed variations correspond to instant changes of distance across the gap.

In one exemplary embodiment of the method, at least one of the positions is generally aligned with an external strand (i.e. a peak or center of the strand) when at least one other of the positions is generally aligned with a groove between external strands, with the positions arranged generally on the same side or opposite sides of the wire rope. Preferably, the positions at which the changes are sensed lie in a common plane transverse to the central axis of the wire rope, and preferably the changes of field strength or magnetic flux are sensed by sensors located at the positions and separated from the central axis of the wire rope by equal distances when the wire rope is free of lateral movement. In one embodiment, the positions at which the changes are sensed number, in total, twice the number of external strands of the wire rope, with the positions being substantially equally angularly spaced around the circumference of the wire rope.

The changes of magnetic flux may be sensed by various kinds of devices, for example Hall effect devices located where the magnetic flux circuit enters or leaves the region of the wire rope, flux gate sensors, or electrical induction coils positioned within the magnetic field surrounding the region of the wire rope. The electrical induction coils may be positioned at points where the magnetic flux circuit enters or leaves the region of the wire rope conducting the magnetic flux, or at any point along the region.

In another exemplary aspect, the invention provides apparatus for measuring lay length of a wire rope having a number of spirally wound external strands with grooves between the strands causing the wire rope to have a spirally grooved outer surface undulating in surface height from a central axis of the wire rope, and having lay length over which each of the strands completes a single circumferential spiral path around the wire rope. The apparatus includes a sensor device having a sensor body defining an elongated passageway enabling the wire rope to be advanced therethrough in a direction of the central axis of the wire rope while permitting limited lateral movements of the wire rope. The sensor device has one or more generators of magnetic flux positioned to create a magnetic flux circuit having a part thereof passing through a region of the wire rope present in the passageway. Sensors are provided on the body capable of sensing changes of magnetic field strength or magnetic flux in the region of the rope caused by variations of proximity of the wire rope to the sensors, the sensors being located at two or more positions spaced circumferentially around the passageway. The sensors generate signals corresponding to the changes sensed at the two or more positions, and the signals each include components due to surface height and components due to lateral movements of the wire rope at the positions. Means (e.g. an electrical circuit) are provided for subtractively combining the signals from the sensors at the at least two positions to eliminate the components due to the lateral movements to produce a combined signal having an oscillating pattern caused by variations of surface height of the wire rope. The apparatus also has means (e.g. an electrical circuit) for associating oscillations in the oscillating pattern with physical distances along the wire rope, and a lay length calculator or display that calculates or displays a distance along the wire rope of a plurality of the oscillations corresponding in number to the number of spirally wound external strands of the wire rope.

In the apparatus, the sensors may be of various kinds, e.g. Hall effect devices, flux gate sensors, or electrical wire induction coils positioned around the passageway. The sensors may lie in a common plane transverse to a longitudinal axis of the passageway and may be separated from a central axis of the passageway by equal distances. In one embodiment, the device has twice as many sensors as external strands of the wire rope used with the apparatus, with a first half of the sensors all connected together and a second half of the sensors all connected together, and with the sensors of the first half alternating with the sensors of the second half around the passageway.

The apparatus may have inwardly (i.e. radially) projecting annular pole pieces at an entrance to and exit from the passageway, the sensors being positioned on or adjacent to one of the pole pieces. Further sensors may also be provided on or adjacent to another (i.e. the second) of the pole pieces, in which case the apparatus may include circuitry for selecting signals from sensors positioned on or adjacent to only one of the pole pieces at a time. In such cases, the sensors provided on or adjacent to the one of the pole pieces and the sensors positioned on or adjacent to the other of the pole pieces may differ in number so that the apparatus may be used with different ropes having different numbers of external strands such that the number of sensors, in each case, may be double the number of the external strands of the wire rope being subjected to the measurement.

In one embodiment, the device of the apparatus is in the form of two halves surrounding the passageway to allow the device to be installed on a wire rope in situ with the rope positioned in the passageway.

In another exemplary aspect, the invention provides a sensor device for measuring lay length of a wire rope. The device comprises a sensor body defining a passageway enabling a wire rope to be advanced there-through in a direction of a central axis of the wire rope while permitting limited lateral movements of the wire rope. The device has one or more generators of magnetic flux within the sensor body positioned to create a magnetic flux circuit having a part thereof passing through a region of a wire rope when present in the passageway, and a plurality of sensors on the body arranged around the elongated passageway, the sensors being capable of sensing changes of magnetic field strength or magnetic flux in the region of a wire rope in the passageway caused by variations of proximity of the wire rope to the sensors and of generating signals corresponding to the sensed changes. The sensors are located at positions spaced circumferentially around the passageway and are interconnected to form two groups of sensors with the sensors of the first group alternating in position around the passageway with sensors of the second group, and with the sensors of the first group all being interconnected to generate signals that are added together and, separately, the sensors of the second group all being interconnected to generate signals that are added together.

The invention is described in further detail with reference to particular embodiments as illustrated in the accompanying drawings.

DETAILED DESCRIPTION OF THE EXEMPLARY EMBODIMENTS

Figure 1:
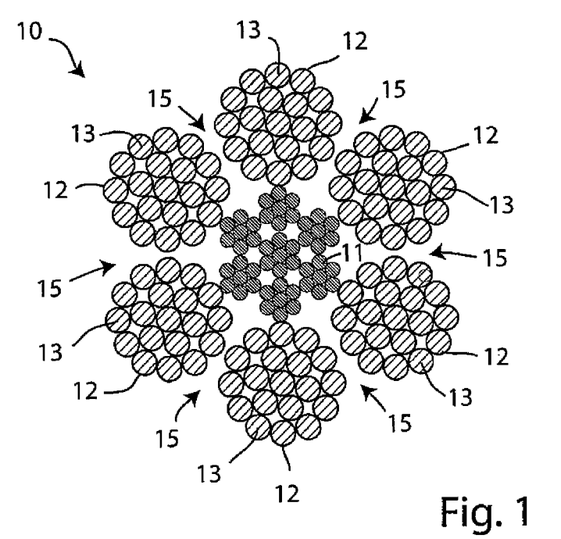
FIG. 1 is a cross-section of a wire rope of a kind typically employed in mining applications.
Figure 2:
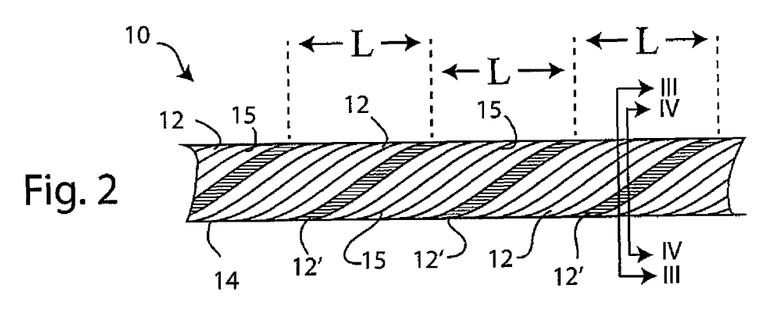
FIG. 2 is a side-view of a wire rope showing the surface pattern provided by external strands and grooves between the strands.

FIGS. 1 and 2 of the accompanying drawings show a cross-section of one form of wire rope 10 having a core strand 11 covered by six spirally wound outer strands 12 typically used for mining operations, although it should be kept in mind that wire ropes of other designs may alternatively be employed, e.g. those having more or fewer external strands, more or fewer core strands 11, and strands of non-circular cross-section. The core strand 11 and the external strands 12 are each made up of bundles of individual metal wires 13 twisted together. As best seen in FIG. 2, the outer surface 14 of the rope is formed by the external strands 12 separated by grooves 15 between the strands, thereby causing the rope to have a spirally grooved outer surface undulating in surface height from the central axis 19 (see FIG. 4) of the wire rope. Each of the external strands 12 twists around the rope in spiral loops separated from each other along the rope by the five other strands 12. In FIG. 2, one strand 12' is provided with a shaded appearance so that its loops can be identified along the rope. The lay length of such a rope is the distance L along the axis or centerline of the rope required for a single strand to complete a single full circumferential spiral path around the wire rope, i.e. to progress around the rope and return to the same angular position at the circumference of the rope. A conventional way of measuring the lay length would be to measure a number of such distances (e.g. the three shown in FIG. 2) using a ruler or similar measuring device, and then to calculate the average of such measurements (dividing by three in the case of FIG. 2).

Figure 3:
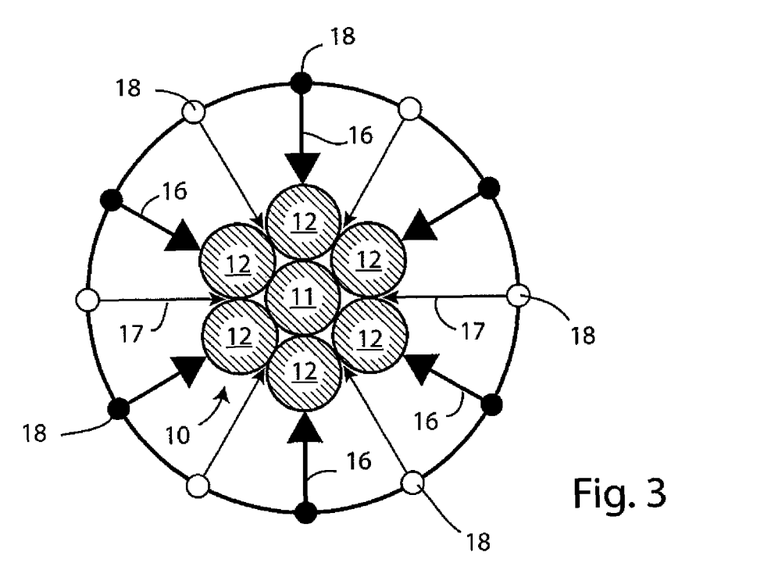
FIG. 3 is a cross-section of a the rope taken on the line III-III of FIG. 2 showing distances from fixed points arranged around the rope.
Figure 4:
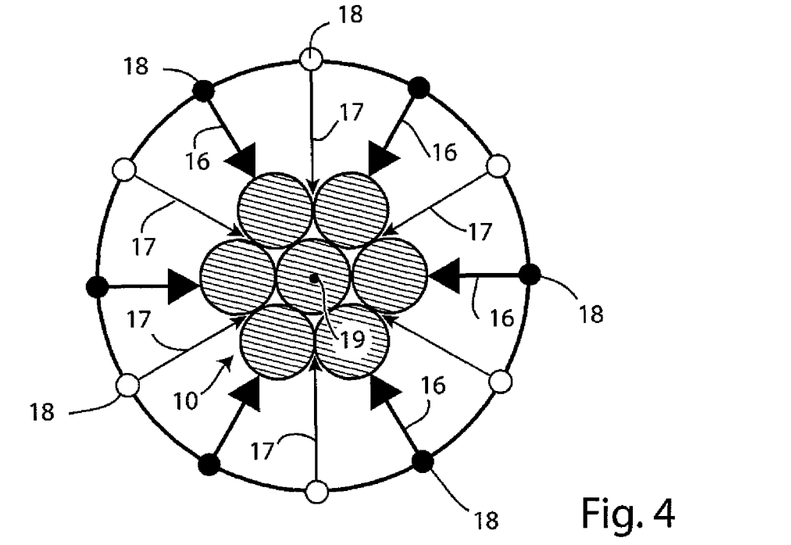
FIG. 4 is a cross-section similar to that of FIG. 3, but taken in the line IV-IV of FIG. 2.

Due to the spirally grooved nature of the outer surface 14 of the rope, the outer surface is made up of peaks formed by the high points of the strands (i.e. the radially outermost or central points) and the grooves 15 between the strands. FIGS. 3 and 4 show the rope 10 at cross-sections and IV-IV, respectively, of FIG. 2. In FIGS. 3 and 4, the peaks of the external strands are shown by large-headed arrows 16 and the grooves are shown by small-headed arrows 17. It will be noticed that the peaks are in a different angular position in FIG. 4 than they are in FIG. 3 due to the fact that the strands 12 have twisted around the center of the rope between the respective axially-spaced cross-sections. Therefore, as the rope advances longitudinally (i.e. along central axis 19) past fixed points of observation in a single cross-sectional plane, the outer surface of the rope moves in an undulating fashion closer to and then further away from the points of observation due to the differences in surface height caused by the peaks and grooves. FIGS. 3 and 4 show such points of observation 18 spaced evenly around the rope 10. If FIGS. 3 and 4 are now taken to represent observations at a single cross-sectional plane of the rope at different times, i.e. the time required for the rope to advance by the distance between cross-sections III and IV of FIG. 2, the points 18 radially aligned with peaks in FIG. 3 (represented by solid circles) become points radially aligned with grooves in FIG. 4 (shown by open circles), and vice versa, as the peaks and grooves move past the fixed points of observation. Proximity sensors positioned at such points of observation would, if sufficiently accurate, record undulating sinusoidal-like variations in distance between the observation points and the outer surface of the rope as the rope advances longitudinally (and without rotation) along its central axis 19. Such sinusoidal variations could potentially be used to measure the lay length of the rope. For example, a measurement of this kind at the topmost point of observation of FIGS. 3 and 4 would provide an oscillating generally sinusoidal output as the rope advances, with the distance of rope advancement causing six such oscillations representing one lay length of the rope. Any six such oscillations along the rope would reveal the lay length at the corresponding positions along the rope, thus showing local lay length measurements, or alternatively, more oscillations over a longer section of the rope (or the entire rope) could be used to provide an average lay length value for that section or for the entire rope.

To associate the oscillations with distances along the rope, means to measure distances of the rope paid out, or means to relate times of measurements to speed of rope advancement, may be employed. However, means for recording rope advancement speed and/or distance are normally provided in equipment used for controlling mining lifts or similar apparatus. For example, rope is often paid out by passing it around a rotating winding wheel, the speed of rotation or number of revolutions of which can be determined conventionally, so that paid-out distances and speeds can be accurately calculated.

Nevertheless, practical difficulties are encountered if attempts are made to use such proximity oscillations to calculate lay length. The first difficulty is that the differences in surface height between the peaks and grooves of the rope are usually quite small, so that the means of measurement must be quite sensitive and unaffected by surface coatings such as grease, dirt, protective coverings, and the like. Secondly, in use, a rope tends to move laterally (off-axis) by considerable amounts as it advances longitudinally, e.g. ropes tend to whip from side to side or to move off-axis due to harmonic lateral oscillations, so the surface of the rope will move towards and away from a fixed point of observation for this reason as well as because of the presence of peaks and grooves in the outer surface of the rope. Such off-axis movements tend to be large in relation to the separation in height between peaks and grooves, and they tend to be irregular and unpredictable, thus making it impossible to observe the regular undulating pattern caused by the peaks and grooves alone.

In one exemplary embodiment of the present invention, these problems associated with lay length measurement are overcome by means and methods based on the generation of a strong magnetic flux within a region of an advancing wire rope. If the wire rope is made of a magnetically permeable metal, such as steel, it is possible to create a strong magnetic flux circuit and to include a region of the rope in the flux circuit. The part of the magnetic flux circuit carried by the wire rope remains longitudinally fixed even as the wire rope is advancing. Such a magnetic flux circuit can be created, for example, by providing strong magnets (e.g. permanent bar magnets) closely spaced around the rope with the positive poles all at one end of the array and the negative poles all at the opposite end. Pole pieces, made for example of magnetically permeable material such as steel, contacting the poles of the magnets at both ends of the array and extending radially inwardly towards the wire rope, help to maximize the magnetic flux within the region of the wire rope extending longitudinally between pole pieces. The magnetic circuit flows through the magnets, through the pole pieces, and through the region of the wire rope between the pole pieces, i.e. the pole pieces form positions where the flux circuit enters or leaves the flux-carrying region of the wire rope. The wire rope does not have to physically touch the pole pieces, and preferably does not, since the magnetic flux is able to span the air gap between each pole pieces and the adjacent surface of the wire rope. The pole pieces are preferably positioned as close to the wire rope as possible without touching it, and may be employed to limit the extent of lateral movements of the wire rope so that signals generated by such movements are correspondingly limited.

The magnetic flux flowing through the affected region of the rope can be utilized in at least two ways to determine the differences of surface height of the rope caused by the spirally grooved outer surface of the rope.

Firstly, the magnetic flux flowing through the region of the rope between the upstream and downstream pole pieces creates lines of magnetic force around the rope, particularly if the wire rope is magnetically saturated. As the surface of the rope moves towards and away from a fixed point due to the presence of the peaks and grooves, the magnetic lines of force also shift towards or away from the fixed point. A magnetic field sensor positioned at such a fixed point is affected by such changes of magnetic field and may generate a measurable electrical voltage or current. For example, a simple magnetic induction coil made of loops of electrically conductive wire positioned parallel to the rope surface will generate a voltage or current when the magnetic field in which it lies varies due to changes of surface proximity. The changes of voltage or current thereby generated will correspond to the changes of distance between the coil and the immediately adjacent (radially aligned) outer surface of the rope due to the moving peaks and grooves of the rope surface as the rope advances, and will thus incorporate an oscillating signal showing those changes of proximity.

Secondly, at the positions where the magnetic flux of the magnetic circuit spans the gaps between the wire rope and the adjacent pole pieces, the strength of the magnetic flux travelling across the gap is affected by the width of the gap, which again varies at points around the pole pieces as the peaks and grooves of the rope surface move past the pole pieces. Thus, a sensor affected by the strength of the magnetic flux will also have an output including an oscillating pattern corresponding to the varying width of the gap.

The variations of magnetic field and magnetic flux sensed in this way are substantially unaffected by coatings on the wire of magnetically impermeable materials, such as grease, dirt and polymer or elastomeric coverings, or the like, and do not rely on physical contact of sensors with the rope surface. However, such variations are also affected by lateral movements of the rope caused by off-axis movements due, for example, to whipping. To neutralize these effects, the exemplary embodiments provide sensors at at least two fixed positions spaced angularly around the wire rope. The fixed positions, and sensors located at such positions, generally all lie in the same plane transverse to the axis of the rope at the same radial distance from the rope axis (when the rope is free of lateral movement), and are located such that one position (or one group of positions) faces a peak of the rope surface when another position (or another group of positions) faces a groove of the rope surface, although the separation of the sensors in this way does not have to be precise. Distance measurements at the two positions (or groups of positions) are generally affected in the same way and at the same time by off-axis movements of the rope, but distance measurements due to the grooved outer surface are "out of phase" at the different positions around the rope (i.e. there is a decrease at one position or group of positions due to the proximity of a groove when there is an increase at another position or group of positions due to the proximity of a peak), and this out-of-phase pattern in the resulting signal remains even if changes of distance due to off-axis movements are eliminated from the measurements at the various positions. If the two sensors located at the fixed positions are close together, they are affected in the same way by off-axis movements of the rope, so the signals from the sensors can simply be subtracted from each other to reveal the oscillating pattern caused by the undulating surface. In other words, the signals are subtractively combined, i.e. combined in such a way that one signal is made positive and the other signal negative as they are combined together.

In one practical embodiment, a plurality of sensors are provided and arranged at fixed positions angularly spaced around the wire rope with the sensors interconnected to form two groups of sensors. The sensors of the two groups are normally alternated in position around the wire rope, i.e. each sensor of the first group is positioned between two sensors of the second group, and vice versa. The signals from the sensors of the first group are additively combined (combined in a positive sense) and signals from sensors of the second group are additively combined to form two signals that are then subtractively combined. The additive combination of signals reinforces or amplifies the signals of each group and makes the desired components of the signals easier to differentiate from background noise. Lateral movements of the rope affect the signals from each of the two groups of sensors in essentially the same way due to the even spacing of the sensors around the wire rope so that the subtractive combination of the signals from the two groups effectively cancels this component.

In a particular embodiment, the number of proximity sensors located around the rope is made twice the number of strands at the surface of the rope, and the sensors are divided into equal two groups, one of which is radially aligned with the peaks (centers) of the external strands when the other is radially aligned with grooves, and vice versa. Hence, at any instant of time as the wire rope advances past the sensors, the sensors of the first group are all radially aligned with points on the surface of the wire rope where the surface height is the same, and all of the sensors of the second group are all radially aligned with points on the wire rope where the surface heights of the wire rope are the same, but the surface heights adjacent the first group of sensors differ from the surface heights adjacent to the second group of sensors most of the time (the surface heights will briefly be the same for both groups of sensors at instants when the sensors of both groups are all positioned approximately mid-way between the peaks and grooves of the wire rope).

The subtractive combination of the signals may be effected by suitable means, e.g. a programmable logic controller, computer or similar calculator, or alternatively, the sensors may all be connected together in a single circuit, but with alternate sets of sensors arranged to generated signals having opposite senses (one set produces a positive signal when the other produces a negative signal) thereby generating a common signal from which the off-axis components have been automatically deleted before delivery of the signal to monitoring apparatus. Such an arrangement combines the functions of additive combination of signals from sensors of the same group and subtractive combination of the signals from the different groups.

When variations of magnetic flux across the gap between the wire rope and pole pieces are used to detect peaks and grooves in the rope surface, it is possible to employ sensors that measure magnetic flux, such as Hall effect sensors and flux gate sensors. These are known devices previously used in this field of technology to measure the metallic area of a wire rope (Hall effect sensors) or wire rope defects (flux gate sensors). Again, a plurality of such sensors is arranged around the rope and signals from two such sensors (or two groups of such sensors) are subtracted to reveal the generally sinusoidal oscillation caused by the undulating surface of the wire rope while eliminating signals caused by lateral (off-axis) movement.

It is found in practice that magnetic induction (wire coil) sensors that sense variations of magnetic field are particularly suited for lay length measurements of wire ropes advancing longitudinally at rapid rates, whereas Hall effect sensors and flux gate sensors that sense changes of magnetic flux across the gap between the rope and the pole pieces may be better suited for lay length measurements at low rates of rope advance.

Figure 5:
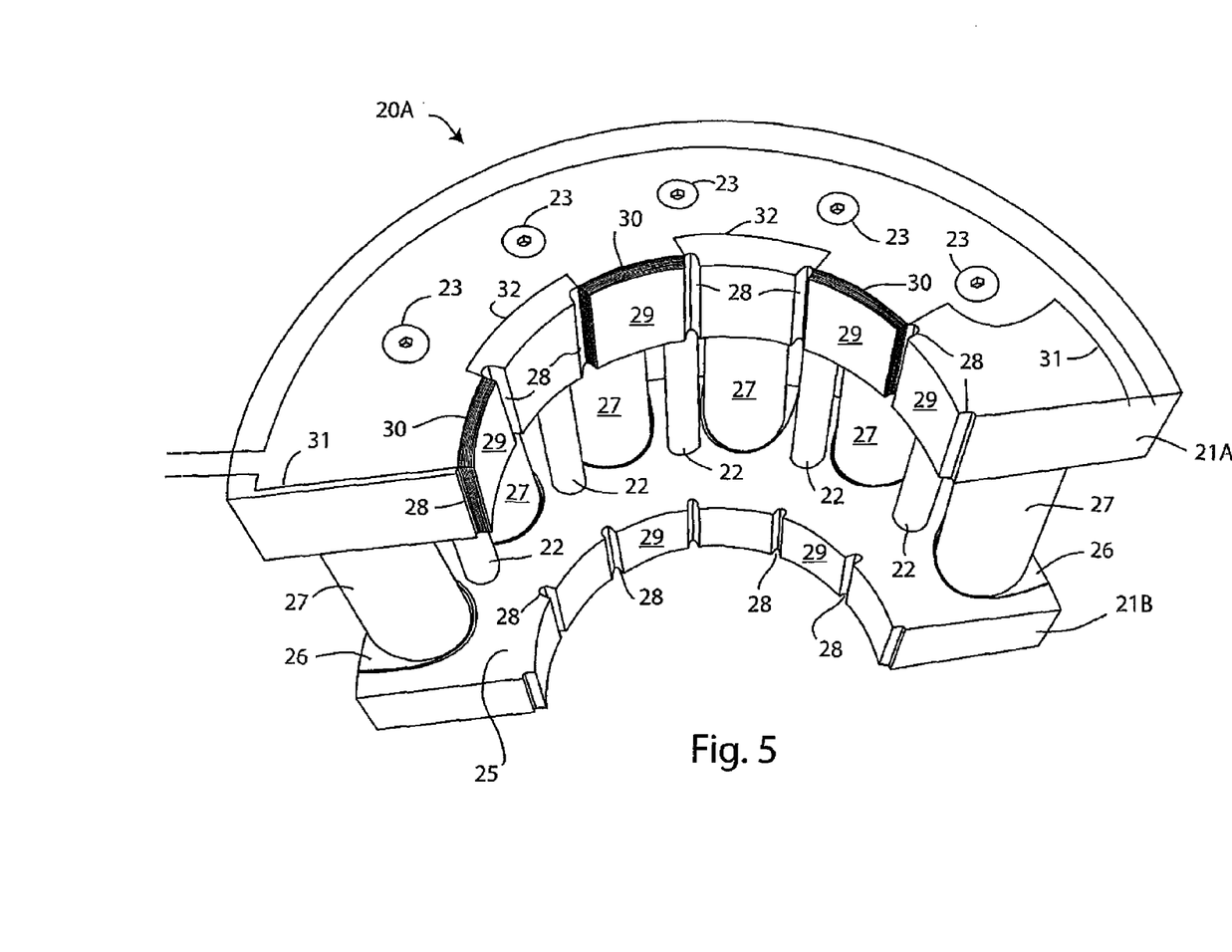
FIG. 5 is a perspective view of a half of a measuring device used for lay length measurement, the half being in an intermediate stage of manufacture.
Figure 6:
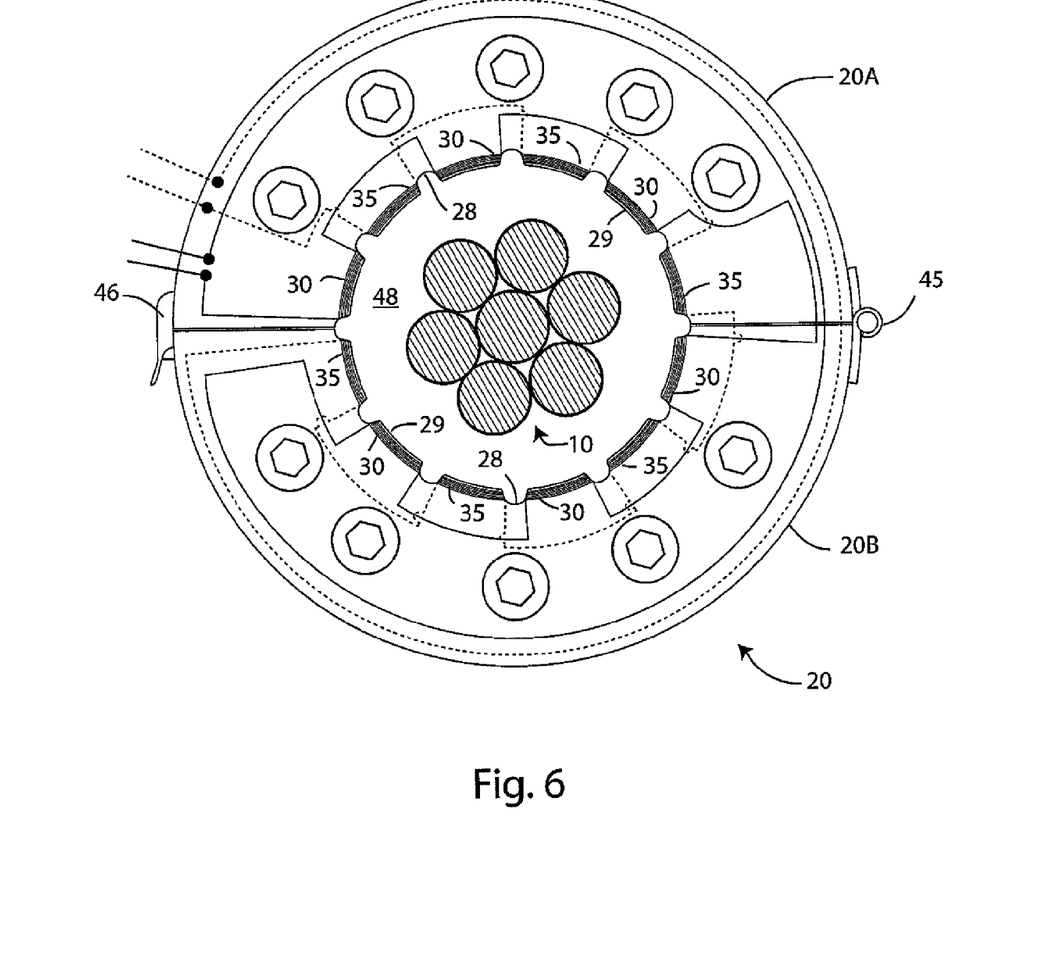
FIG. 6 is a plan view of a completed measuring device made up of two halves, each being similar to the half of FIG. 5.

One exemplary embodiment of apparatus for measuring lay length of a metal rope is shown in FIGS. 5 and 6 of the accompanying drawings. FIG. 5 illustrates one half 20A of a sensor device 20 shown at an intermediate stage of manufacture, and FIG. 6 illustrates in plan view of an assembled sensor device 20, made of two halves 21A and 21B positioned together and surrounding a wire rope 10. It will be seen from FIG. 6 in particular that the sensor device 20 defines a central elongated passageway through which a wire rope 20 may advance in the axial direction of the rope with the possibility of lateral (off-axis) movements.

As illustrated in FIG. 5, the half 20A of the sensor device 20 forms a body supporting two pole pieces 21A and 21B, made for example of steel, separated from each other and fixed in place by rod-like supports 22 attached by screws 23. The upper surface 25 of the lower pole piece 21B has six semi-elliptical depressions 26 extending inwardly from an outer edge, and the lower surface (not visible) of the upper pole piece 21A has similar semi-elliptical depressions aligned with those below. These depressions guide and position six cylindrical permanent magnets (not visible) held within external mounting tubes 27 so that the ends of the magnets directly contact the pole pieces 21A and 21B. The components of the sensor device other than the magnets and pole pieces are preferably made of non-magnetic material such as aluminum. The permanent magnets in tubes 27 and pole pieces 21A, 21B create a magnetic flux circuit that is completed by the region of the metal wire rope 10 extending longitudinally between the pole pieces. The part of the magnetic flux circuit passing through this region of the rope remains in place despite the advancement of the wire rope through the sensor device 20.

In the illustrated embodiment, the inside surfaces of the pole pieces 21A, 21B are provided with short radial grooves 28. The parts of the pole pieces between these grooves in effect form inwardly facing gear-like projections 29. In the upper pole piece 21A, the projections 29 are wound with copper wire to form magnetic induction sensing coils 30. Only three such coils 30 are shown in FIG. 5 and these are formed on alternate projections 29 (thus, if the projections are numbered consecutively 1, 2, 3, 4, 5 and 6 around the central passageway, only the odd projections 1, 3 and 5 are provided with coils at this stage). These coils are joined together by wires 32 to form a common circuit. At the next stage of production of the sensor device half 21A, coils 35 (see FIG. 6) are provided on the remaining three projections 29 (i.e. the even projections 2, 4 and 6), with such coils being electrically interconnected to form a common circuit, but a circuit separate from that formed by the coils already installed on the odd projections. In the assembled sensor device shown in FIG. 6, coils 30 and 35 surround the wire rope 10 and are connected to form two separate electrical circuits (one formed by the "odd" coils 30 and the other formed by the "even" coils 35). A similar half 20B of the sensor device 20 is wired in an equivalent way and the two halves are assembled to produce a cylindrical sensor device 20 as shown in FIG. 6. In this figure, the wire circuit joining the odd coils is shown in solid lines whereas the wire circuit joining the even coils is shown in dashed lines so that the circuits can be easily distinguished. It can be seen that, when the coils 35 of the dashed line circuit all align radially with peaks of the metal rope surface (as shown in FIG. 6), the coils 30 of the solid line circuit face grooves, and vice versa, as the rope advances through the sensor device. For the illustrated wire rope 10 having six external strands, the sensor device has twelve induction coil sensors 30, 35, i.e. double the number of surface strands, arranged in two separate circuits.

The coils 30, 35 act as induction coils that generate electrical voltages and/or currents when cut through by moving electrical fields. The magnetic flux passing through the region of the wire rope 10 within the sensor device 20 creates a generally tubular magnetic field through and around the rope and, as the surface of the metal rope approaches or recedes from a coil (due to the strands forming spiral peaks and grooves at the surface of the rope, and off-axis movement of the rope through the measurement device), varying electric voltages or currents are induced in the coils. All the coils of one circuit (e.g. the dashed line circuit) experience the same or similar current induction because the peaks or grooves formed by different strands of the wire rope all approach or recede from these coils at the same time and in the same way. The same is true of the coils of the second circuit (e.g. the solid line circuit), but the currents in the two groups of coils are out of phase with each other. For example, when peaks are approaching the coils of the dashed line circuit, the coils of the solid line circuit are sensing a surface that is receding into a groove. The electrical signals produced by coils of the dashed line circuit all reinforce each other to produce a stronger signal output. Likewise the electrical signals of the coils of the solid line circuit all reinforce each other and produce a stronger signal output. Electrical induction caused by lateral off-axis movement, such as rope whipping, affects each circuit at the same time and in the same way. The changes in the output signals of the two circuits produced by whipping or other lateral movements are thus similar in the outputs of the two circuits and can be subtracted and the remaining signals combined to reveal the underlying oscillating generally sinusoidal pattern produced by the peaks and grooves of the wire rope surface.

Figure 7A:
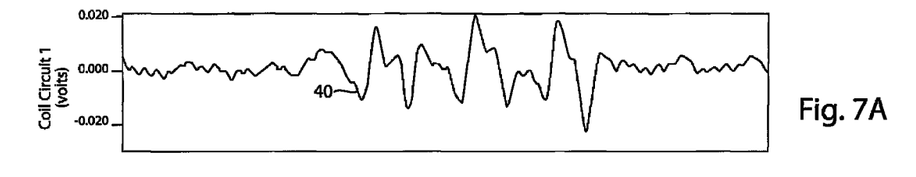
FIGS. 7A, 7B, 7C and 7D are charts showing, respectively, the output from one coil circuit, the output from a second coil circuit, the outputs from the two coil circuits subtracted, and lay length measured at points along a wire rope.
Figure 7B:
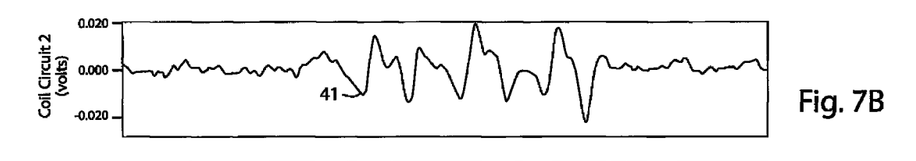
Figure 7C:
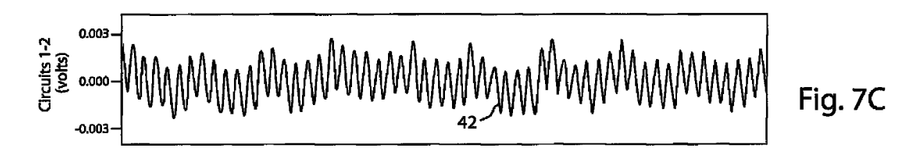
Figure 7D:
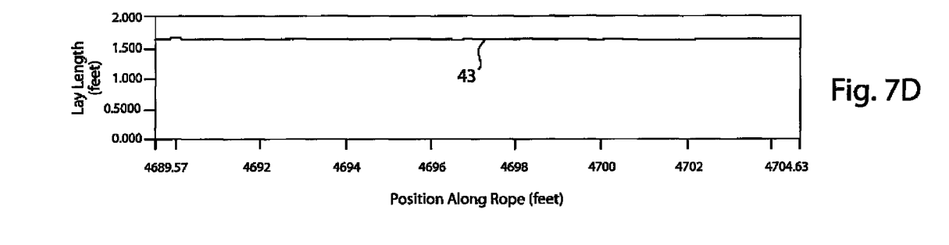

FIGS. 7A to 7D show typical induction signal outputs from two such circuits and the way in which the information in these signals can be manipulated to reveal the patterns caused by surface height variation, and thus the lay length of the wire rope. FIG. 7A shows the output 40 from one of the coil circuits (e.g. the dashed line circuit) and FIG. 7B shows the output 41 from the other of the circuits (the solid line circuit). The plots show signal electrical voltage against distance along the rope (measured by rope speed or distance meters, not shown). These outputs from the two circuits are of similar appearance but the oscillations are displaced slightly from each other along the horizontal axis. If the signals are subtracted from each other, the result is a sinusoidal-like signal 42 as shown in FIG. 7C. The peaks and grooves along this trace represent the peaks and grooves in the surface of the wire rope "seen" by the coils. As the rope has six external strands at the surface, the distance between six oscillations therefore represents one lay length of the rope passing through the measurement device. The position of such a part of the wire rope, or its speed of advance, is generally known from the winding apparatus used for paying out the rope, and this can be used to reveal the lay length of the rope at that position. The calculation of lay length obtained in this way can be carried out automatically and continuously by a suitable circuit device, e.g. by a programmable logic controller or the like, to generate a chart such as the one shown in FIG. 7D where the vertical axis represents lay length and the horizontal axis represents distance along the wire rope. The plot 43 shows the calculated lay length at positions along the rope. Hence, any changes in lay length become clearly apparent and the sections of the rope exhibiting such changes are revealed from the plots. Incidentally, such lay length profiles of a wire rope generated at different times and stored in memory may subsequently be superimposed on each other to reveal changes of lay length over time. The results have been found to be so accurate and reproducible that if measurements are carried out on a specific rope at short intervals of time, the osciallating traces thereby obtained are substantially identical and may even reveal regular repeating changes of lay length cause by rope overlay on the winding drum (local stretching where the rope completes one layer on the drum and is then raised over that layer to form a new layer).

The sensor device 20 shown in FIG. 6 is, as already explained, made in two device halves 20A and 20B. This design allows the device to be opened and positioned around a wire rope 10 while the rope is in situ in winding apparatus. The two halves are joined together at one side by one or more hinges 45 and are held in place on the other side by releasable latches 46. The device is normally mounted on a fixed piece of a winding apparatus, e.g. immediately below a winding wheel in the winding shack where rope whipping is usually at a minimum. In order to allow the measurement device to be opened without affecting the coil circuits, the connections between wires of the halves 20A, 20B are positioned close to hinge 45 and are provided in the form of a jumper cable (not shown) with enough slack to allow the device to be fully opened without causing breakage of the wires. External connection points for the circuits may be located on the side of the device opposite to the hinge near the latch 46, as shown.

Although not shown for reasons of clarity, the sensor device may be enclosed and protected in various ways. In a particular embodiment, the central passageway 48 through the device is provided with a protective tube, made in two halves like the device itself, that extends from one of the pole pieces to the other and covers the outer ends of the projections 29 and the coils 30, 35. Such a tube is made of non-magnetic material, e.g. a tough plastics material, so that it does not attenuate the magnetic flux or magnetic field significantly. The wire rope then passes through the center of the tube that consequently protects the device against contact with the wire rope should off-axis movement become excessive. Similarly, protective plastic or metal end plates may be used to cover the outer ends of the pole pieces and a tubular shell, again in two halves, may enclose the exterior of the device.

While, in the above embodiment, the coils 30, 35 are connected to form two separate circuits that generate separate outputs subsequently subjected to subtraction, an alternative embodiment connects all of the coils together, but reverses the direction of winding of one coil relative to the next. Thus, the coils on all of the odd-numbered projections 29 may all have a clockwise direction of winding (as seen from the center of the measurement device), and the coils on the even-numbered projections may all have an anti-clockwise direction of winding. Magnetic field changes passing through such coils thereby cause signals of opposite voltage or current to form in the coils of opposite winding direction. Hence the voltage signals of adjacent coils tend to cancel out, except for the differences caused by the out of phase signals induced by the varying surface height (peaks and grooves) of the rope surface. Nevertheless, the components of the signals from coils having windings in the same direction are amplified, so the oscillating component in the output signal is amplified and easy to distinguish from background noise. Thus, such an embodiment produces a combined signal that has already undergone subtraction of the components produced by off-axis movement of the rope, such as caused by rope whipping and the like, and amplification of the components due to changes of surface height of the wire rope.

Also, in the embodiment of FIGS. 5 and 6, only the upper pole piece 21A is provided with coils 30, 35, even though the lower pole pieces 21B is also provided with grooves 28 gear-like projections 29. In an alternative embodiment, the lower pole 21B piece may also be provided with further coils in the same manner as the upper pole piece 21A to act as a safeguard in case the upper coils are damaged or undergo failure. In such an embodiment, only the coils of one pole piece would be employed at any time to produce lay length measurement signals, i.e. circuitry is provided for selecting signals from the sensors on one of the pole pieces or the other. In another alternative embodiment, the projections of the lower pole piece may be made to differ in number from those of the upper pole piece and all be provided with coils.

For example, the lower pole piece may have sixteen projections and coils connected into two circuits, while the upper pole piece would have twelve projections and coils as shown in FIG. 6. This would make the sensor device particularly suitable for use with a rope having eight external strands (when the coils of the bottom pole piece would be monitored) as well as a rope having six external strands (when the coils of the upper pole piece would be monitored). The resulting device is therefore more versatile.

Similar signal outputs to those shown in FIGS. 7A to 7D would be obtained with measurement devices relying on measurements of flux variations across the gaps between the rope and pole pieces, e.g. Hall effect devices or flux gate sensors.

Figure 8:
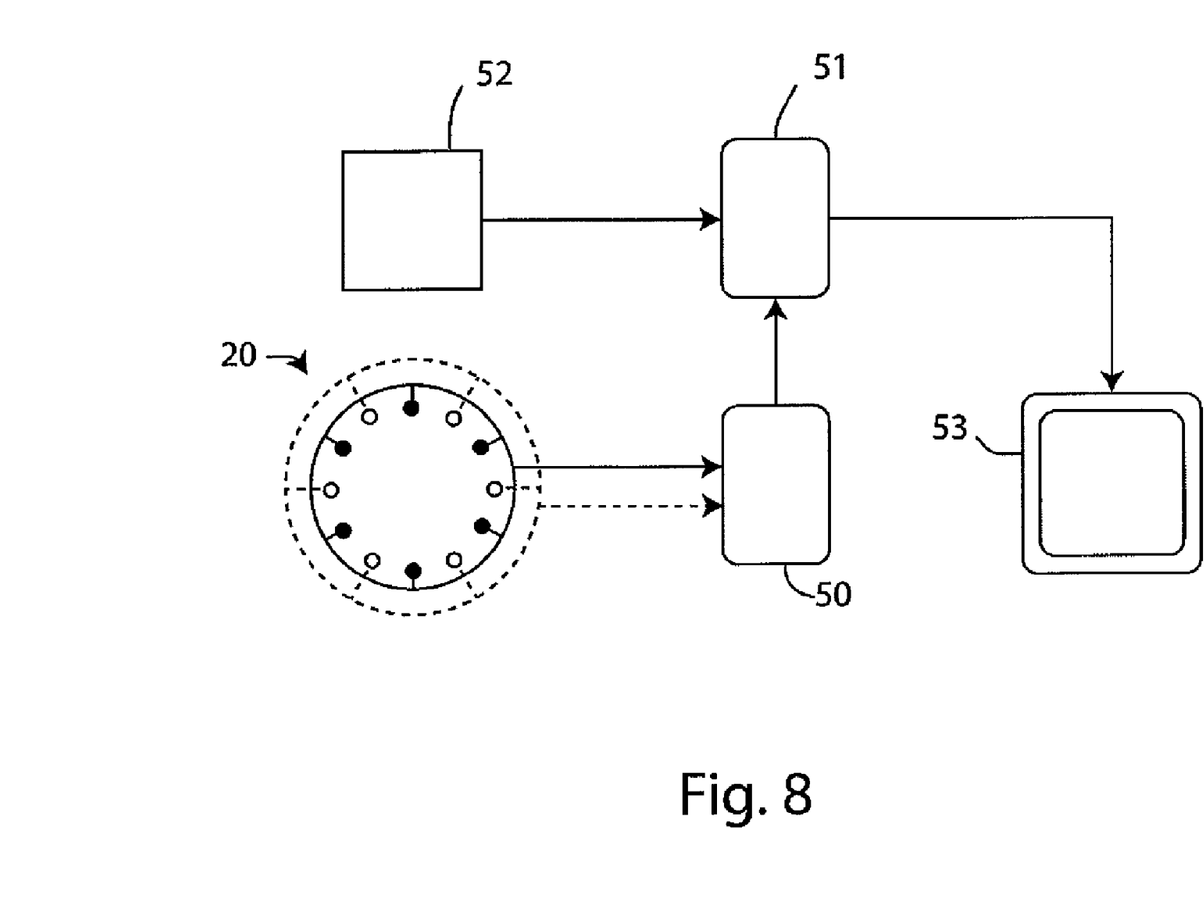
FIG. 8 is a simplified schematic diagram of apparatus according to one embodiment of the invention showing interconnection of various parts thereof.

FIG. 8 of the accompanying drawings shows in schematic form how parts of the apparatus of FIGS. 5 and 6 may be interconnected in one exemplary embodiment of the invention. The signals from the two groups of sensors in the sensor device 20 feed to a circuit 50 for subtractively combining the signals to eliminate components due to transverse movements of the wire rope (not shown in this figure) and a combined signal is generated and forwarded to a further circuit 51. A device 52 measures distances of wire rope paid out and fed through the sensor head 20, and a corresponding signal is fed to circuit 51 so that the combined signal from circuit 50 is associated with distances along the wire rope. The signals so associated are fed to a calculator and display element 53 to calculate lay length of the wire rope at positions there along and to display the result. The result may also be recorded in this or a separate unit for replay and analysis. In embodiments where the sensors are electrical induction coils with alternating sensors wired in opposite senses and all connected together, the circuit 50 is eliminated because the wiring of the sensors creates a combined signal from which components due to transverse motion of the wire rope have been eliminated.

While the sensor device as described includes circuitry for subtracting the signals and calculating or displaying lay length of the rope, the sensor body itself may be sold as a separate component of the apparatus. The body may include the generators of magnetic flux and supporting apparatus, the sensors arranged around the central passageway, and wiring for interconnecting the sensors to form two groups of sensors either having separate signal outputs, or a single combined output if the sensors are of a kind that generate signals of opposite sense.

The invention claimed is:

1. A method of measuring lay length of a wire rope, comprising:

advancing a wire rope in a direction of a central axis of the rope while permitting limited transverse movements of the wire rope, the wire rope having a number of spirally wound external strands with grooves between the strands causing the rope to have a spirally grooved outer surface undulating in surface height from the central axis, and having lay length over which each of the strands completes a single circumferential spiral path around the central axis of the wire rope;

establishing a magnetic flux circuit, part of which magnetic flux circuit occupies a region of the advancing wire rope;

sensing changes of magnetic field strength or magnetic flux in said region of the wire rope due to variations of proximity of the wire rope from fixed positions spaced circumferentially around the wire rope, said positions being radially aligned with points on said wire rope at which the surface heights of the wire rope differ due to said undulating surface, and generating signals corresponding to changes of magnetic field or magnetic flux sensed at said positions, the signals each including components due to surface height and components due to lateral movements of the wire rope at said positions;

subtractively combining the signals to eliminate the components due to the lateral movements to produce a combined signal having an oscillating pattern caused by differences of surface height at said positions;

associating oscillations in the pattern with physical distances along the wire rope; and establishing, as the lay length, a distance along the wire rope of a plurality of said oscillations corresponding in number to the number of spirally wound external strands of the wire rope.

2. The method of claim 1, wherein said changes of magnetic field strength or magnetic flux are sensed at more than two said positions spaced circumferentially around the wire rope, the positions forming a first group, all of the positions of which are radially aligned with points on the wire rope where the surface heights are the same, and a second group, all of the positions of which are radially aligned with points on the wire rope where the surface heights are the same but differ from the surface heights at the points radially aligned with the positions of the first group, and wherein the signals generated at the positions of the first group are added together and the signals generated at the positions of the second group are added together to form two signals that are then subtractively combined to form said combined signal.

3. The method of claim 2, wherein said positions of said first group are all aligned with external strands of said wire rope when said positions of said second group are all aligned with grooves in said outer surface of the wire rope.

4. The method of claim 1, wherein the positions at which the changes are sensed all lie in a common plane transverse to the central axis of the wire rope.

5. The method of claim 1, wherein the changes of field strength or magnetic flux are sensed by sensors located at said positions and separated from the central axis of the wire rope by equal distances when the wire rope is free of lateral movement.

6. The method of claim 1, wherein the positions at which the changes are sensed number, in total, twice the number of external strands of the wire rope, the positions being substantially equally angularly spaced around the circumference of the wire rope.

7. The method of claim 1, wherein the changes of magnetic flux are sensed by Hall effect devices located where the magnetic flux circuit enters or leaves said region of the wire rope.

8. The method of claim 1, wherein the changes of magnetic flux are sensed by flux gate sensors.

9. The method of claim 1, wherein the changes of magnetic field strength are sensed by magnetic induction coils positioned within a magnetic field surrounding the region of the wire rope.

10. The method of claim 9, wherein the magnetic induction coils are positioned where the magnetic flux circuit enters or leaves the region of the wire rope.

11. An apparatus for measuring lay length of a wire rope having a number of spirally wound external strands with grooves between the strands causing the wire rope to have a spirally grooved outer surface undulating in surface height from a central axis of the wire rope, and having lay length over which each of the strands completes a single circumferential spiral path around the wire rope, the apparatus comprising:
- a sensor device having a sensor body defining an elongated passageway enabling the wire rope to be advanced therethrough in a direction of the central axis of the wire rope while permitting limited lateral movements of the wire rope, the sensor device having one or more generators of magnetic flux positioned to create a magnetic flux circuit having a part thereof passing through a region of the wire rope when present in the passageway;
- sensors on the body capable of sensing changes of magnetic field strength or magnetic flux in said region of the rope caused by variations of proximity of the wire rope to the sensors, the sensors being located at two or more positions spaced circumferentially around the passageway, the sensors generating signals corresponding to said changes sensed at the two or more positions, such that the signals each include components due to surface height and components due to lateral movements of the wire rope at said positions;
- means for subtractively combining the signals from the sensors at the at least two positions to eliminate the components due to the lateral movements to produce a combined signal having an oscillating pattern caused by surface height of the wire rope;
- means for associating oscillations in the oscillating pattern with physical distances along the wire rope; and
- a lay length calculator or display that calculates or displays a distance along the wire rope of a plurality of the oscillations corresponding in number to the number of spirally wound external strands of the wire rope.

12. The apparatus of claim 11, having more than two of said sensors spaced circumferentially around the passageway, the sensors forming a first group and a second group with the sensors of the first group alternating in position around the passageway with sensors of the second group, and with the sensors of the first group interconnected to generate signals that are added together and the sensors of the second group are interconnected to generate signals that are added together, thereby forming said two signals that are subtractively combined by said circuit for subtractively combining said signals.

13. The apparatus of claim 12, wherein the sensors of the first group are positioned to align radially with external strands of a wire rope passing through said passageway when the sensors of the second group are radially aligned with grooves of said undulating external surface of the wire rope.

14. The apparatus of claim 11, wherein the sensors lie in a common plane transverse to a longitudinal axis of the passageway.

15. The apparatus of claim 11, wherein the sensors are separated from a central axis of the passageway by equal distances.

16. The apparatus of claim 11, having twice as many sensors as external strands of a wire rope intended to be used with the apparatus.

17. The apparatus of claim 11, wherein sensor device includes radially inwardly projecting annular pole pieces at an entrance to and exit from the passageway to facilitate magnetic flux passage into or removal from said region of wire rope in the passageway, the sensors being positioned on or adjacent to one of said pole pieces.

18. The apparatus of claim 17, wherein additional sensors are also provided the other of the pole pieces, the apparatus including circuitry for selecting signals from sensors positioned on or adjacent to only one of said pole pieces at a time.

19. The apparatus of claim 18, wherein sensors provided on or adjacent to the one of the pole pieces and the sensors positioned on or adjacent to the other of the pole pieces differ in number to selectively measure lay lengths of different wire ropes having different numbers of external strands from each other.

20. The apparatus of claim 11, wherein the sensor device is in the form of two separable halves surrounding the passageway to enable the sensor device to be installed around a wire rope with the rope positioned in said passageway.

21. The apparatus of claim 11, wherein the sensors are Hall effect devices.

22. The apparatus of claim 11, wherein the sensors are flux gate sensors.

23. The apparatus of claim 11, wherein the sensors are induction coils.

24. The apparatus of claim 12, wherein said sensors are magnetic induction coils formed of electrical wire wound into coils having a clockwise or anti-clockwise winding direction, the winding direction of the coils of the first group all being the same, and the winding direction of the coils of the second group all being the same but opposite to that of the sensors of the first group, the electrical coils all being interconnected in a single circuit functioning, due to said opposite winding directions of the induction coils of the first and second groups, as said circuit for subtractively combining said signals, the output of which is said combined signal.

25. A sensor device for measuring lay length of a wire rope, the device comprising:
- a sensor body defining a passageway enabling a wire rope to be advanced therethrough in a direction of a central axis of the wire rope while permitting limited lateral movements of the wire rope;
- one or more generators of magnetic flux within the sensor body positioned to create a magnetic flux circuit having a part thereof passing through a region of a wire rope when present in the passageway; and
- a plurality of sensors on said body arranged around said elongated passageway, said sensors capable of sensing changes of magnetic field strength or magnetic flux in the region of a wire rope in said passageway caused by variations of proximity of the wire rope to the sensors and of generating signals corresponding to said sensed changes;
- wherein the sensors are located at positions spaced circumferentially around the passageway and are interconnected to form two groups of sensors with the sensors of the first group alternating in position around the passageway with sensors of the second group, and with the sensors of the first group interconnected to generate signals that are added together and the sensors of the second group interconnected to generate signals that are added together.

26. The device of claim 25, wherein the sensors lie in a common plane transverse to a longitudinal axis of the passageway.

27. The device of claim 25, wherein the sensors are separated from a central axis of the passageway by equal distances.

28. The device of claim 25 having twice as many sensors as external strands of a wire rope intended to be used with the device.

29. The device of claim 25, wherein sensor device includes radially inwardly projecting annular pole pieces at an entrance to and exit from the passageway to facilitate magnetic flux passage into or removal from said region of wire rope in the passageway, the sensors being positioned on or adjacent to one of said pole pieces.

30. The device of claim 29, wherein additional sensors are also provided on the other of the pole pieces, the device including circuitry for selecting signals from sensors positioned on or adjacent to only one of said pole pieces at a time.

31. The device of claim 30, wherein sensors provided on or adjacent to the one of the pole pieces and the sensors positioned on or adjacent to the other of the pole pieces differ in number to selectively measure lay lengths of different wire ropes having different numbers of external strands from each other.

32. The apparatus of claim 25, wherein the sensor body is in the form of two separable halves surrounding the passageway to enable the sensor device to be installed around a wire rope with the rope positioned in said passageway.

33. The apparatus of claim 25, wherein the sensors are Hall effect devices.

34. The apparatus of claim 25, wherein the sensors are flux gate sensors.

35. The apparatus of claim 25, wherein the sensors are induction coils.

36. The apparatus of claim 25, wherein said sensors are magnetic induction coils formed of electrical wire wound into coils having a clockwise or anti-clockwise winding direction, the winding direction of the coils of the first group all being the same, and the winding direction of the coils of the second group all being the same but opposite to that of the sensors of the first group, the electrical coils all being interconnected in a single circuit.

* * * * *